United States Patent [19]

Alsop

[11] Patent Number: 5,024,952
[45] Date of Patent: Jun. 18, 1991

[54] METHOD FOR OBTAINING ANALYTES FROM LIQUID MENSTRUA FOR ANALYSIS

[75] Inventor: George M. Alsop, South Charleston, W. Va.

[73] Assignee: Union Carbide Chemicals and Plastics Technology Corporation, Danbury, Conn.

[21] Appl. No.: 371,112

[22] Filed: Jun. 26, 1989

[51] Int. Cl.$^5$ ........................ G01N 1/18; G01N 35/08; G01N 30/00; C02F 1/30

[52] U.S. Cl. ........................................ 436/177; 436/52; 422/68.1; 210/748

[58] Field of Search ................................ 436/177–178, 436/52; 422/68.1, 186, 306; 55/7, 8, 10, 46; 210/748

[56] References Cited

U.S. PATENT DOCUMENTS

| | | | |
|---|---|---|---|
| 1,069,169 | 8/1913 | Parker . | |
| 3,465,500 | 9/1969 | Fenn . | |
| 3,633,027 | 1/1972 | Rykage . | |
| 3,912,470 | 10/1975 | Fluckiger . | |
| 3,936,374 | 2/1976 | Bradley et al. . | |
| 4,198,297 | 4/1980 | Valdes-Krieg et al. | 210/704 |
| 4,271,291 | 6/1981 | Dayvolt | 210/703 |
| 4,289,594 | 9/1981 | Alpaugh et al. . | |
| 4,314,906 | 2/1982 | Dunn et al. . | |
| 4,421,651 | 12/1983 | Burkholder et al. . | |
| 4,437,999 | 3/1984 | Mayne . | |
| 4,464,343 | 8/1984 | Hitchcock et al. | 210/704 |
| 4,511,444 | 5/1986 | Caporiccio et al. . | |
| 4,512,900 | 4/1985 | Macur et al. . | |
| 4,559,808 | 12/1985 | Sturman | 436/177 |
| 4,582,629 | 4/1986 | Wolf . | |
| 4,600,559 | 7/1986 | Hiatt . | |
| 4,935,209 | 6/1990 | Pfoutz | 55/8 |

FOREIGN PATENT DOCUMENTS

| | | | |
|---|---|---|---|
| 521970 | 9/1979 | Australia . | |

OTHER PUBLICATIONS

"Reduction in Sample Foaming in Purge and Trap Gas Chromatography/Mass Spectrmetry Analyses", M. E. Rose et al., *Analytical Chemistry,* vol. 51, 2176–2180; 2177, col. 1, FIG. 1.

"The Adsorptive Bubble Separation Techniques (the adsubble techniques) , Foam Fractionation and Allied Processes", Lemlich, Robert, *Chemical Abstracts, vol. 86, No. 18, May 2, 1977, see p. 348, Abstract 126850w.*

Traces Heavy Met. Water Removal Processes Monit., Proc. Symp. 1973, 211–223 (Eng.).

"Optimization of a Gas Stripping Concentration Technique for Trace Organic Water Pollutants", *Chemical Abstracts,* vol. 93, No. 6, Aug. 11, 1980, B. Colenutt et al., see p. 436, Abstract 53574s, Int. J. Environ. Anal. Chem. 1980, 7(3), 231–244 (Eng.).

"Test Methods for Evaluating Solid Waste, Physical/-Chemical Methods", U.S. Environmental Protection Agency, SW-846, 3rd Edition.
"Adsorptive Bubble Separation Techniques", Academic Press, New York, N.Y. (1972), R. Lemlich, Editor.

"Monodisperse Aerosol Generation Interface for Combining Liquid Chromatography with Mass Spectroscopy", Willoughby et al., *Analytical Chemistry,* vol. 56, 2626–2631 (1984).

(List continue on next page.)

*Primary Examiner*—David L. Lacey
*Assistant Examiner*—Jan M. Ludlow
*Attorney, Agent, or Firm*—Norman L. Balmer; Henry H. Gibson

[57] ABSTRACT

Solutes are obtained from liquid menstrua by bubbling gas through the liquid menstrua wherein solute passes to the interface between the bubble and the liquid menstrum and/or into the gas within the bubble. The bubble breaks the surface of the liquid menstruum and defines an entrainment zone which is subjected to electromagnetic radiation to maintain solute in the vapor space. The recovered solute may, for instance, be subjected to analytical analysis.

30 Claims, 2 Drawing Sheets

"Performance of an Improved Monodisperse Aerosol Generation Interface for Liquid Chromatography/Mass Spectrometry", Winkler et al., *Analytical Chemistry*, vol. 60, 489–493 (1988).

U.S. Environmental Protection Agency Method 8240, "Gas Chromatography/Mass Spectrometry for Volatile Organics", Sept. 1986.

Supelco 1989 Catalogue No. 27, p. 240.

Abstract 1482 for the Paper, "Utilization of Multi-Bed, Carbon-Based Absorbent Tubes for Adsorption and Subsequent Thermal Desorption of Volatile, Semi-Volatile and Non-Volatile Organic Compounds Sparged from Environmental Sample", Betz et al., presented March 6–10, 1989, 40th Pittsburgh Conference and Exposition on Analytical Chemistry and Applied Spectroscopy, Atlanta, Ga.

*Peak*, Summer 1988, p. 4.

"Determination of Parts-Per Billion Concentrations of Dioxane in Water and Soil by Purge and Trap Gas Chromatography/Mass Spectrometry or Charcoal Tube Enrichment Gas Chromatography", Epstein, et al., *Analytical Chemistry*, vol. 59, No. 15, 1987–1990 (1987).

"Gas Chromatographic Analysis of Beer Flavor Compounds", Chen, *Brew Dig.*, vol. 60, No. 11, 30–32 (1985).

METHOD FOR OBTAINING ANALYTES FROM LIQUID MENSTRUA FOR ANALYSIS

This invention pertains to methods and apparatus for recovering analytes, or solutes, from liquid menstrua, especially for analytical procedures in which the analyte is detected in respect of its presence and/or relative content.

BACKGROUND TO THE INVENTION

A frequently conducted analytical procedure is the determination of the presence and/or relative amount of certain chemical compounds in samples in which, if the chemical compound is present, may be in a relatively small amount, e.g., in the parts per billion or less range. These analytical procedures may be conducted, for instance, to analyze water or soil for the presence and/or relative amount of organic pollutants such as aliphatic or aromatic compounds such as benzene, chlorobenzene, phenanthrene, anthracane, polychlorinated biphenyls, trichloroethane, naphthalene, and the like. In conducting these environmental analyses, because of the small amount of the analyte present and the possible deleterious effect of massive amounts of the medium containing the analyte on the analytical detection means, it is generally desired to concentrate the analyte or remove it from the medium or provide it in a suitable medium for the analysis. For example, soil samples cannot be directly used for mass spectroscopy or gas chromatography analyses. The large amount of water in water samples may overpower mass spectrometers or gas chromatographs.

Any analytical method for determining analytes in, e.g., soil or water samples should be repeatable, i.e., the analytical technique should not introduce undue sample-to-sample variations. Moreover, it should be relatively non-complex and require minimal time and effort to conduct. If, for instance, a plot of land is to be inspected for potential contamination, the greater the number of soil samples analyzed, the greater the assurance that an accurate representation of the condition of the land will be achieved. With more labor intensive, longer duration analytical procedures, analytical costs may become very significant, especially for large plots of land.

Because of the importance of analytical protocol in the arena of environmental evaluations, the United States Environmental Protection Agency has issued during September, 1986, Method 8240 entitled "Gas Chromatography/Mass Spectrometry for Volatile Organics". The scope of the method is stated to be useful ... to determine volatile organic compounds in a variety of solid waste matrices. This method is applicable to nearly all types of samples, regardless of water content, including ground water, aqueous sludges, caustic liquors, acid liquors, waste solvents, oily wastes, mousses, tars, fibrous wastes, polymeric emulsions, filter cakes, spent carbons, spent catalysts, soils and sediments. (Page 8240-1).

Method 8240 contemplates the likelihood that analytes may have to be recovered from samples prior to being introduced into, e.g., a gas chromatograph. These methods include a purge-and-trap process:

An inert gas is bubbled through the solution at ambient temperature, and the volatile components are efficiently transferred from the aqueous phase to the vapor phase. The vapor is swept through a sorbent column where volatile components are trapped. After purging is completed, the sorbent column is heated and backfiltered with inert gas to desorb the components onto a gas chromatographic column. (Page 8240-6).

For sediment/soil and waste samples, an extraction method, among others, is recommended. See, for instance, *Test Methods for Evaluating Solid Waste, Physical/Chemical Methods,* SW-846, Third Edition, United States Environmental Protection Agency.

In one currently practiced method for the determination of organic compounds in environmental samples, the original matrix (such as soil, water, sludge, etc.) is treated by liquid-liquid extraction with an organic solvent, e.g., methylene chloride, hexane, 2-propanol, cyclohexane or acetonitrile to remove organic compounds. The extraction is for a period of 18 to 24 hours. The sample may then be dried and subjected to further treatment by solvent exchange. See Method 3520, September 1986. Method 640, September, 1986, disclosed a gel-permeation technique for clean-up. Both the above Methods are contained in the above Environmental Protection Agency document. This extract can be introduced into the analytical instrument such as a gas chromatograph/mass spectrometer. The sample preparation procedure often takes up to 72 hours to complete.

It is not uncommon to encounter emulsions during an extraction procedure involving an aqueous sample. This may make difficult, if not impossible, separation of the organic phase and can result in a loss of sensitivity due to a partial loss of the organic compounds. Another problem that can be encountered occurs when the sample contains heavy organic residues. The extract will contain the organic residues and can lead to fouling of the analytical system. The fouled system must be cleaned to remove the residue build-up. Methods do exist for removing the heavy organic residue from the samples; however, such procedures require time and effort and may result in a partial loss of the organic compounds sought to be detected by the analytical system. One procedure for cleaning an extract containing heavy organic residues involves a gel-permeation technique such as disclosed in Method 3640 discussed above.

For purposes of gas chromatography/mass spectroscopy, analytes are generally placed into two categories: volatiles and semivolatiles. Current analytical protocols specify different procedures for analytes in each category. Hence, two sample preparations may be required to cover organic compounds in both categories.

Supelco Equipment Co. markets a Dynamic Thermal Stripper for purging volatile or nonvolatile organic compounds from samples for analytical evaluation. Page 240 of Supelco's 1989 Catalogue No. 27 bills the dynamic thermal stripper as "Replace Tedious Liquid-Liquid Extractions, Thermal Stripper Ensures Efficient Recovery of Many Compounds". The unit is depicted as having a sample vial through which a purge gas is bubbled. The sample vial is contained within a heated airbath oven (30° to 200° C.). The effluent from the sample vial is passed to a thermal desorption tube in a heatable jacket. In the catalogue description, Supelco states:

Organics in aqueous solutions are recovered through steam distillation. This allows the compounds to be volatilized and transported to the adsorbent tube at temperatures well below their boiling points. Thus, sample breakdown is prevented. To prevent water vapor in the effluent from condensing in the tube, dry gas is added to the distilled samples and the adsorbent tube is heated. This ensures efficient trapping of the organic molecules.

The use of steam distillation, as noted by Supelco, mandates procedures for the removal of substantial amounts of water which is carried overhead. The use of the adsorbent may still enable a substantial amount of water to be retained. Moreover, the adsorbent can affect the quality of the analysis since different analytes may interact with the adsorbent differently. Supelco presented a paper at the 40th Pittsburgh Conference and Exposition on Analytical Chemistry and Applied Spectroscopy held in Atlanta, Ga., during the week of Mar. 6–10, 1989 (Betz, et al., "Utilization of Multi-Bed, Carbon-Based Absorbent Tubes for Adsorption and Subsequent Thermal Desorption of Volatile, Semivolatile and Nonvolatile Organic Compounds Sparged from Environmental Samples".) According to the authors:

Volatile, semivolatile, and nonvolatile organic contaminants in environmental sample matrices (water, wastewater, soil, etc.) are usually prepared for chromatographic evaluation through different techniques. Typically, volatile compounds are prepared by purge and trap methods, and semivolatile and nonvolatile compounds are prepared by liquid-liquid extraction. Multi-bed adsorbent tubes containing several nonspecific, carbon-based, Class I adsorbents have been constructed. These tubes effectively adsorb and subsequently thermally desorb the volatile, semivolatile, and nonvolatile fractions sparged (steam distilled) from aqueous sample matrices. When interfaced with a dynamic thermal stripper and a thermal desorber unit, these tubes permit simultaneous analysis of all three contaminant fractions. This adsorbent tube/instrumentation system eliminates the tedious sample preparation, and other shortcomings, associated with recovery methods incorporating a combination of purge and trap and liquid-liquid extraction.

Nonspecific Class I adsorbents adsorb compounds according to molecular size and shape, thus eliminating concern over which functional group(s) an adsorbate possesses. Because these adsorbents are also hydrophobic, competition for the adsorbent surface favors the analytes of interest during steam distillation. Utilization of four Class I adsorbents, each having a different surface area, allows the adsorbent tube to function in a size-exclusion operating mode. These adsorbents include two graphitized carbon blacks and two carbon molecular sieves.

The organic contaminants are steam distilled by using the thermal dynamic stripper. This unit transfers the organic contaminants from the sample matrix to the adsorbent tube by shifting the system equilibrium to favor the vapor phase. Following adsorption, the adsorbates are effectively transferred to a gas chromatograph via the thermal desorber unit. This unit interfaces with both packed and capillary columns, hence several analytical columns may be chosen.

Work reported by R. Lemlich, Editor, *Adsorptive Bubble Operation Techniques;* Academic Press, New York, N.Y. (1972) relates that, due in part to surface energy considerations, compounds such as organic compounds tend to be at a higher concentration at the interface of an aqueous medium and a gas than in the aqueous medium as a whole. By bubbling a gas through the aqueous medium, organic compounds tend toward the interface, and when the bubble breaks the surface, it carries with it some of the aqueous medium surrounding the bubble. The organic compound may be at the interface or in the vapor space in the bubble.

This phenomenon has been referred to as the "adsorptive bubble separation" technique and can be found in nature, e.g., in sea foam and bubbling marshes, as well as in everyday life. Lemlich and coworkers studied the phenomenon using crystal violet chloride as a solute in water and much work was done studying the effect of vessel height, diameter, bubble size and retention on the separation. Lemlich noted at page 141 of the above book that chemical additives can enhance separation, e.g., replacing distilled water with tap water in the crystal violet chloride/water system increased the separation ratio fivefold and the addition of sodium sulfate increased the separation ratio to more than 50. At page 142, Lemlich notes that the addition of certain volatile organic compounds to the gas improves the selectivity of separation.

The adsorption bubble separation technique differs from flotation separation techniques used, for instance, in the paper and mining industries. In the flotation separation technique, bubbles of gas are used to bring a disparate phase, e.g., solids, to the surface of a liquid (see, for instance U.S. Pat. No. 1,069,169). Foams may be used to stabilize the disparate phase.

U.S. Pat. No. 4,314,906 discloses a water purification technique in which water is chlorinated, halogenated organic compounds are produced as a result of the chlorination, and then the halogenated organic compounds are removed by aeration. A carbon filter is used by the patentees to remove any trace amounts of halogenated organic compounds remaining in the water after aeration. The concept of reacting chemical species in liquids and then removing them by, e.g., aeration, or by gas evolution, is also used in ozonation processes such as disclosed in U.S. Pat. Nos. 4,437,999; 4,512,900 and 4,591,444. In, for instance, U.S. Pat. No. 4,437,999, ozone is sparged through a liquid containing organic resin or biological matter while subjecting the liquid to ultraviolet light. The organic material reacts with the ozone to produce water and carbon dioxide. At column 4, lines 48, et seq., the patentees state:

As is known, ultraviolet light facilitates and enhances the oxidation action of ozone and has an incidental heating effect that causes evaporation of some of the quantity of water, which is increasing by the development of water as a product of oxidation of the organic material.

The patentees then suggest that the rate of evaporation of the water be equivalent to the rate of production of water through the oxidation reactions.

In U.S. Pat. No. 4,512,900, the patentees note that in the ozone/ultraviolet light purification method disclosed in U.S. Pat. No. 4,289,594, the presence of surfactants in the liquid caused foaming. Hence, initially the ozone was bubbled through slowly (with the surfactants forming a film of liquid surrounding the bubbles) until the ozone had oxidized the surfactant. Then more vigorous ozonation could occur. The patentees disclose pretreating the liquid with hydrogen peroxide to eliminate undue amounts of surfactant prior to the ozone/ultraviolet light treatment.

U.S. Pat. No. 4,582,629 discloses the use of microwave energy to separate oil and water emulsions. The patentee states that the microwave treatment can be used in conjunction with the separating and heating devices such as skimmers, gun barrel treaters, heater treaters, and the like. U.S. Pat. No. 4,421,651 discloses energizing a molecular sieve adsorbent column with directionally applied microwave energy to produce a mixed gas and liquid effluent. The gas is said to promote the discharge of effluent from the column bottom.

SUMMARY OF THE INVENTION

By this invention methods and apparatus are provided for removing, or extracting, at least one solute from a liquid menstruum in a manner which does not require the undue volatilization of the liquid menstruum. The methods and apparatus of this invention are particularly suitable for recovering analytes from samples such as soil, water, sludges, residues, etc., for analytical evaluation by, for instance, gas chromatography, infrared spectroscopy, liquid chromatography and mass spectroscopy. Moreover, sample preparation can be relatively simple and requires little time or effort.

In a broad aspect of the invention, a gas is passed in the form of finely divided bubbles through a liquid menstruum containing at least one solute intended to be recovered wherein the temperature of the liquid menstruum is below its boiling point; the bubbles pass into an immediately adjacent vapor space and entrain at least a portion of the liquid menstruum at the interface between the menstruum and gas bubbles; and at least the portion of the vapor space containing entrained liquid menstruum is irradiated with electromagnetic radiation which is capable of imparting energy to the at least one solute in an amount sufficient to maintain at least a portion of the at least one solute contained in the entrained liquid menstruum in the vapor space. A vapor stream containing the gas passed through the liquid menstruum and the at least one solute can be withdrawn from the vapor space and, e.g., subjected to an analytical procedure to ascertain at least one of presence and relative content of the at least one solute. Advantageously, the radiation source for the irradiation of the vapor space is proximate to the vapor space.

In a further broad aspect of the invention, apparatus are provided for the extraction, or removal, of at least one solute from a liquid menstruum comprising a vessel adapted to contain the liquid menstruum in a region and define a vapor space above the liquid menstruum; means for introducing gas in the form of finely-divided bubbles into the region of the vessel adapted to contain the liquid menstruum; radiation means adapted to introduce electromagnetic radiation into the vessel in at least a region of the vapor space immediately above the liquid menstruum, said radiation means capable of energizing the at least one solute to maintain at least a portion of the solute in the vapor space; and outlet means from said vessel adapted to enable a vapor stream comprising the gas provided by the means for introducing the gas and at least one solute to pass from the vessel. The outlet means may be in communication with a conduit for passing the vapor stream to an analytical system, either directly or with further concentration and/or purification. The conduit may also direct the vapor stream to means for removing the at least one solute from the vapor stream.

In a further broad aspect of apparatus in accordance with this invention, methods for analyzing a liquid menstruum in respect of at least one solute wherein a gas is sparged through the liquid menstruum to provide a vapor stream comprising the gas and at least a portion of the at least one solute, and at least a portion of the vapor stream is subjected to analytical analysis, wherein the at least one solute has a significantly higher molecular weight than each of the gas and the liquid menstruum, the improvement comprising passing the vapor stream through a momentum separator to concentrate the at least one solute in the vapor stream before the analytical analysis.

DISCUSSION

The methods of this invention can have wide applicability as techniques for separating at least one component from another liquid component. Thus, the methods may be advantageous for the removal of solutes from liquid menstrua for the purpose of, for instance, purifying the liquid menstrua, obtaining a more concentrated analyte sample containing the solute, recovering solute, or separating one solute from another solute contained in the liquid menstrua.

The relationship between the at least one component to be removed and the liquid menstruum is one in which the concentration of the at least one component tends to be greater at the interface of the liquid menstruum with a gas than in the liquid menstruum as a whole. Accordingly, different solutes and liquid menstrua provide different types of surface energies that enhance the tendency of the desired solute or solutes to concentrate at the interface. As is well recognized, the nature of the gas at the interface with the liquid menstruum can also influence the surface energies at the interface and provides another parameter by which the tendency of the desired solute to concentrate at the interface can be achieved.

Hence, more hydrophobic components in polar media will normally tend to be forced toward the interfaces with gases. Generally, the more polar the media, the greater the propensity of hydrophobic components to be driven to these interfaces. With hydrophobic media, polar molecules tend to concentrate at the interface with the bubbles; however, the driving force typically tends to be weaker than that when the polar molecules form the media and hydrophobic molecules are concentrated at the interface. The polarity of the gas bubbles through the menstruum can have some effect on the surface energies at the interface, but due to the differences in densities between the liquid and gas, these effects tend to be relatively minor in respect to the surface energy effect.

The solutes which are removed in accordance with the methods of this invention are most frequently organic compounds including, but not limited to, aromatic and aliphatic hydrocarbons (e.g., of 1 to about 30 carbon atoms); oxygenated hydrocarbons including aliphatic and aromatic ethers, alcohols, carboxylic acids and esters, and carbonyls (e.g., of 1 to about 30 carbon atoms); sulfur-containing hydrocarbons such as thioethers, mercaptans, sulfonyls and sulfonic acids and esters (e.g., of 1 to about 30 carbon atoms); nitrogen-containing compounds such as amines, imines, cyanates, quaternary ammonium salts, ureas and urethanes (e.g., of 1 to about 30 carbon atoms); phosphorus-containing compounds such as phosphines, phosphonic acids and esters, and phosphoryls (e.g., of 1 to about 30 carbon atoms); and halogenated compounds, e.g., with one or more of fluorine, chlorine, bromine and iodine, of, say, the above mentioned classes of hydrocarbon-containing compounds. Exemplary of solutes are acenaphthylene, acenaphthene, acetone, acetophenone, acrolein, acrylonitrile, anthracene, benzene, benzo(A)anthracene, benzo(A)pyrene, bis-(2-chloroethyl) ether, bis-(2-ethylhexyl)phthalate, biphenyl, biphenyl ether, bromochloromethane, bromodichloromethane, 4-bromofluorobenzene, bromoform, bromomethane, 2-butanone, butylated hydroxytoluene, carbon disulfide, carbon tetrachloride, chlorobenzene, chlorodibromomethane, chloroethane, 2-chloroethyl vinyl ether, chloroform, chloromethane, chrysene, cresol, dibromomethane, dibutylphthalate, 1,2-dichlorobenzene, 1,4-dichloro-2-butene, dichlorodifluoromethane, 1,1-dichloroethane, 1,2-dichloroethane, 1,1-dichloroethene, trans-1,2-dichloroethene, 1,2-dichloropropane, cis-1,3-dichloropropene, trans-1,3-dichloropropene, diethylphthalate, 1,4-difluorobenzene, di-n-octylphthalate, 1,4-dioxane, dioxins, ethanol, 2-ethoxyethanol, ethylbenzene, ethyl methacrylate, fluoranthrene, fluorene, fluorophenol, fluorobiphenyl, 2-hexanone, indenopyrenes, iodomethane, methylene chloride, methyl naphthalene, 4-methyl-2-pentanone, naphthalene, nitrobenzene, phenanthrene, phenol, polychlorinated biphenyls, Polybrominated biphenyls, propylbenzenes, pyrene, styrene, terphenyl, 1,1,2,2-tetrachloroethane, tetrahydronaphthalene, tetrachloroethane, toluene, 1,2,4-trichlorobenzene, 1,1,1-trichloroethane, 1,1,2-trichloroethane, trichlorofluoromethane, 1,2,3-trichloropropane, vinyl acetate, vinyl chloride, and xylenes.

The liquid menstrua useful in accordance with the methods of this invention may be organic or inorganic and may be wholly miscible with the solute to be removed or the solute may have limited solubility in the liquid menstruum. Often, the solubility of the solute in the liquid menstruum is at least about 0.0001 gram per liter at 25° C., e.g., about 0.001 to 250, say, 0.01 to 100, grams per liter at 25° C. It may not be essential that the material of the solute be entirely dissolved in the liquid menstruum. Rather, the solubility enables the solute to be transported to the interface between the menstruum and the bubbles. Hence, the material of the solute may be a solid which has limited solubility in the liquid menstruum and is dissolved, under steady state conditions, at a rate approximating the rate of removal of the solute from the liquid menstruum. Indeed, the solute may be introduced into the liquid menstruum as an adsorbed species on a solid sorbent. The organic liquid menstrua include by way of illustration, lower alcohols, e.g., methanol, ethanol, n-propanol, i-propanol and n-butanol; lower carboxylic acids and esters, e.g., formic acid, acetic acid, propionic acid and acetylacetonate; carbonyls such as acetone, acetaldehyde, methylethylketone and crotonaldehyde; halogenated hydrocarbons, e.g. methylene chloride, and hydrocarbons such as hexane, cyclohexane, benzene, toluene, xylene, cyclohexane, oils, and the like. Most preferably, the solutes are hydrophobic or contain hydrophobic moieties and the menstruum is more polar than the solutes to be removed. In many instances, the solute to be removed is contained in an aqueous medium. Hence, water is a common liquid menstruum.

The amount of the solute in the liquid menstruum can vary widely. The methods of this invention, however, are particularly advantageous as compared to, e.g., distillation, when the solute is present in relatively small amounts, e.g., less than one gram per liter, e.g., as little as 0.001 parts per million by weight or less.

The methods of this invention may find desirable utility in removal of solutes from waste water, ground water, aqueous sludges, aqueous residues and from liquid mixtures prepared from solid or semi-liquid samples, e.g., from soil, food, body fluid, medicinal, and biological samples in a suitable liquid menstruum.

The liquid menstruum containing the solute may be suitable as received, e.g., ground water, or may require preparation. For instance, soil samples may be provided in an aqueous medium in ground form and the medium agitated to enhance the transfer of the solute to the liquid phase. Slurries and highly viscous liquids may have additional solvent added to reduce viscosity and facilitate achieving smaller gas bubble sizes (i.e., more interfacial surface areas per unit volume of the gas).

The liquid menstruum may also contain transfer-enhancing agents. Two of the classes of transfer-enhancing agents useful in the processes of the invention include additives which enhance the driving force to concentrate the solute at the bubble interfaces and additives which decrease bubble size. The transfer-enhancing agents may be a combination of both. A first class of transfer-enhancing agents appears to operate by enhancing the tendency of the solute to be at a higher concentration at the interface of the liquid menstruum with a gas, e.g., by reducing the solubility of the solute in the liquid menstruum or by enhancing the rate that a solute in a solid enters the liquid menstruum. A second class of transfer-enhancing agents promotes the formation of finely divided bubbles of the gas, i.e., decreases the size of the gas bubbles. Representative transfer enhancing agents are inorganic salts such as sodium sulfate and calcium chloride, and organic compounds such a n-butanol, nonionic surfactants, anionic surfactants, cationic surfactants and polyethylene glycols. Agents such as sodium sulfate have been proposed for purge and trap-type analytical procedures. See, for instance, Epstein, et al., "Determination of Parts-per-billion Concentrations of Dioxane in Water and Soil by Purge and Trap Gas Chromatography/Mass Spectrometry or Charcoal Tube Enrichment Gas Chromatography", *Analytical Chemistry*, Vol. 59, No. 15, 1987-1990 (1987).

A wide variety of gases may find utility in various methods in accordance with the invention. As the gas can affect the surface energy of the liquid menstruum at the interface, care should be taken not to select a gas which unduly reduces the tendency of the solute to be removed from becoming more concentrated at the interface. Often, the polarity of the gas and its solubility in the liquid menstruum will be key parameters influencing the surface energies and the tendency of the solute to be more concentrated at the interface. Representative gases include helium, nitrogen, oxygen, air, xenon, fluorine, chlorine, bromine, ammonia, phosphine, carbon monoxide, carbon dioxide, sulfur dioxide, and nitrogen oxides, e.g., nitrogen oxide, nitrogen dioxide, nitrous oxide. For analytical processes, inert gases such as helium may often be preferred whereas for water detoxification, air may be preferred due to economic considerations.

The gas is preferably passed through the liquid menstruum in finely divided form, e.g., the desired average bubble size is less than about 10 or 20 millimeters in diameter. Small bubble sizes are generally preferred due to the greater interfacial surface areas per unit volume of gas. Accordingly, devices which assist in nucleating bubbles of smaller sizes are often used. Frequently, the average bubble size ranges from about 0.1 millimeter to 10 millimeters. Larger bubble sizes, however, can be used. The pressures under which the processes of this invention are operable may vary widely from subatmospheric to superatmospheric pressure, e.g., often from about 0.01 to 50 atmospheres absolute, and most frequently from about 0.25 to 5 atmospheres absolute. For the sake of convenience and avoiding undue volatilization of the liquid menstruum, the pressures typically approximate ambient pressure, for instance, 0.9 to 1.2 atmospheres absolute.

The bubbles may be introduced via a sparge tube, by vortex action caused by agitation, by vaporization of liquid or rapid expansion of compressed gas, by vaporization of a dissolved component and/or by ultrasound and bubble plates (e.g., frit plates).

The contact time between a gas bubble and the liquid menstruum can vary widely depending upon the scale of the operation and the presence of a means for retaining the bubbles within the liquid menstruum. Thus, the contact time may vary from less than 0.01 second to greater than 30 seconds. Often, the average contact time is from about 0.05 to 30 seconds.

The duration of the bubbling of the gas through the liquid menstruum is generally chosen to either recover a desired amount of solute or remove a desired amount of solute from the liquid menstruum. Factors such as the driving force of the solute to the interface, the size of the bubbles, the contact time of the bubbles with the liquid menstruum, and the uniformity of the dispersion of the bubbles throughout the liquid menstruum will each have an effect on the rate of removal of the solute from the liquid menstruum. The duration of passing the gas through the liquid menstruum may be relatively short for analytical procedures, e.g., for a sufficient time to provide sufficient sample containing solute for conducting the analysis. This duration may be as little as 15 or 30 seconds and may be for periods of up to 24 hours. For methods in which the amount of recovery of solute or the removal of solute from the liquid menstruum is an objective, the duration of passing the gas through the liquid menstruum is typically longer, e.g., at least about one hour, say, about 1 to 200, for instance, 6 to 100, hours.

The bubbles desirably break the surface of the liquid menstruum with sufficient velocity to entrain at least a portion of the liquid menstruum at the interface with the bubble. (Some of the solute at the interface may pass into the gas within the bubble and therefore be in the vapor phase as the bubble breaks the surface of the liquid menstruum.) It is generally preferred that the amount of foaming caused by the bubbling be minimized if not essentially avoided. Two methods that have been proposed for avoiding foaming during Purge-and-trap analytical procedures are the addition of a defoaming agent such as a silicone defoamer and heat dispersion of any generated foam. See, for instance, Rose, et al., "Reduction in Sample Foaming in Purge and Trap Gas Chromatography/Mass Spectrometry Analyses", *Analytical Chemistry*, Vol. 51, No. 13, 2176–2180 (1979).

The entrained liquid carried by the bursting bubbles passes into the vapor space above the liquid menstruum and is irradiated to provide energy to the solute molecules to maintain them in the vapor space. The wavelength range of the radiation is advantageously chosen for its ability to impart energy to the solute molecules. In some instances, the frequency which imparts energy to the solute molecules does not impart as much energy to the molecules of the liquid medium. Hence, by selection of appropriate radiation frequencies, enhanced separations, i.e., concentrations, of the solute from the liquid medium can be achieved. The radiation can be electromagnetic radiation including, but not limited to, those frequencies associated with radio frequencies, microwaves, infrared, visible light, ultraviolet and x-rays. Frequently, the radiation is within the infrared region of the spectrum, i.e., 0.6 micron to 50 microns in wave length, where the solute is an organic.

Imparting energy to the solute in the vapor space generates heat, i.e., solute molecules in the vapor space achieved a sufficiently high temperature to be maintained in the vapor space. However, the methods of this invention do not provide sufficient heat to the liquid menstruum that an undue amount of the menstruum is vaporized. Often, the temperature of the liquid menstruum is at least about 10° C., preferably at least about 20° C., and sometimes at least about 40° C., below its boiling point under the conditions in the vapor space. For the purposes herein, reference to a boiling point will be with reference to the conditions in the vapor space including the effect of pressure and the presence of other components in the vapor space. Often, the temperature of the liquid menstruum is between about 0° and 80° C., say, 15° to 60° C.

For many applications, especially qualitative analytical procedures, only a low percentage of the solute being entrained into the vapor space need be maintained in the vapor space yet advantageous results can still be obtained. Thus, the operator has considerable flexibility in providing sufficient radiation to enable solute to be retained in the vapor space but yet not overly heat the liquid menstruum. Optionally, the radiation may be concentrated in the vapor space to minimize the radiant heating of the liquid menstruum. For instance, the liquid menstruum may be shielded from the radiation. Another technique for maintaining the liquid menstruum below its boiling point is to introduce direct or indirect cooling into the menstruum. By way of illustration, an indirect cooling coil can be placed in the liquid menstruum or the gas being passed through the liquid menstruum may be chilled.

Although the methods of this invention provide a greater mole ratio of the solute to the material of the liquid medium in the vapor space than that ratio in the liquid menstruum, in many instances further concentration or selective recovery may be desirable. Numerous techniques are available for such concentration of selective recovery. For instance, the solute or the material of the liquid medium may be selectively absorbed or adsorbed or condensed. Representative absorbents include water, amines, halocarbons, oxygenated hydrocarbons, and hydrocarbons. Representative adsorbents include activated carbon, silica gel, molecular sieves, alumina, and magnesia. Condensation (liquification) may be effected by coalescing from the vapor phase, condensing on a cool surface, and freezing on a cool surface. The condensation may be selective or may be non-selective with the desired separation being effected by selective vaporization (e.g., flashing or simple or fractional distillation) or in the case of freezing, by selective liquification or vaporization. Useful condensation apparatus include cryogenic concentrators which may operate at temperatures at which the solutes become solids. In operation, after collection of the components on the cryogenic concentrator surface, the surface is heated to release the components in a more concentrated form, e.g., in a carrier gas for, say, analytical processing. The use of cryogenic concentrators, or cryogenic focusing apparatus, has been suggested for purge-and-trap analytical procedures. See, for instance, U.S. Pat. No. 4,600,559 and Chen, "Gas Chromatographic Analysis of Beer Flavor Compounds", *Brew Dig.,* Vol. 60, No. 11, 30–32 (1985).

Another technique which is particularly attractive for analytical sample preparations in which the solute (analyte) has a significantly higher molecular weight than the molecular weights of the material of the liquid menstruum, and the gas which is passed through the liquid menstruum is separation by momentum separation. In a momentum separator, molecules pass from one orifice through an open space toward another orifice while a force (e.g., gravity and/or vacuum and/or shock waves and/or centrifugal force) draws lighter molecules away from a projected path. The molecules with the greater mass (and hence greater momentum) can pass from one orifice to another whereas those with lesser mass are deflected by the force and do not enter the opposing orifice. By selection of the magnitude of the force, the distance between the orifices, and the geometry of the orifices, concentrating the analyte can be relatively effective. Momentum separators have been used in conjunction with mass spectrometers. *Peak,* Summer 1988, page 4, discloses a particle beam separator in which a nebulized stream of helium, solvent vapor and analyte are passed through a two-stage momentum separator in which solvent vapor is drawn away by vacuum. Momentum separators have been proposed by separation of hydrogen, nitrogen, methane, ammonia and other gases from heavier components. See, for instance, U.S. Pat. Nos. 3,465,500; 3,633,027; 3,912,470, and 3,936,374, Willoughby, et al., "Monodisperse Aerosol Generation Interface for Combining Liquid Chromatography with Mass Spectroscopy", *Analytical Chemistry,* Vol. 56, 2626–2631 (1984) and Winkler, et al., "Performance of an Improved Monodispense Aerosol Generation Interface for Liquid Chromatography/Mass Spectrometry", *Analytical Chemistry,* Vol. 60, 489–493 (1988).

Membranes through which volatilized liquid menstruum can pass may also be used to concentrate the solute-containing stream. Noij, et al., in "Selective Removal of Water in Purge-and-cold-trap Capillary Gas-chromatographic Analysis of Volatile Organic Traces in Aqueous Samples", *J. High Resolut. Chromatogr. Chromatog. Commun.,* Vol. 10, No. 2, 60–66 (Feb., 1987) suggest that a Nafion TM membrane be used to remove water to prevent blocking of the capillary cold trap.

The amount of solute removed from the liquid menstruum will vary widely depending upon the intended purpose for which the removed solute will be used. For instance, for analytical measurements, the portion of the solute removed may be relatively minor but in an amount sufficient to effect the analytical procedure. When the methods of this invention are intended to purify a liquid menstruum, or recover the solute, e.g., as a product, the portion of the solute removed may approach 100 percent. The methods often enable a substantial amount of the at least one solute to be recovered, e.g., usually at least about 20, e.g., say, at least about 30, e.g., 30 to 99, or more percent of the at least one solute in the liquid menstruum to be recovered.

The concentrated or recovered solute may be further processed as desired. For instance, the solute may be a reactant and recycled to the reaction zone. It may be undesired and can be disposed of more readily in the concentrated form such as by incineration, chemical reaction to render it inert, or waste storage. It may also be a desired product and can be more readily recovered in a salable form. Another use is as a sample for analytical analysis. The sample can be passed to a detection means and because of its greater concentration than in the liquid menstruum, better analytical results may ensue. Suitable detection means include chromatographic apparatus including gas chromatographs and liquid chromatographs; raman spectrometers; mass spectrometers; atomic adsorption spectrometers, and infrared spectrometers. Another type of analytical device involves the reaction or absorption of the analyte such as wet chemical methods (titrametric, gravimetric, electrophoresis, chromatographic, colorimetric, etc.) and biological assay or immunoassay tests with a material that, e.g., changes color or electrical conductivity when the reaction or absorption occurs.

Figure 1:
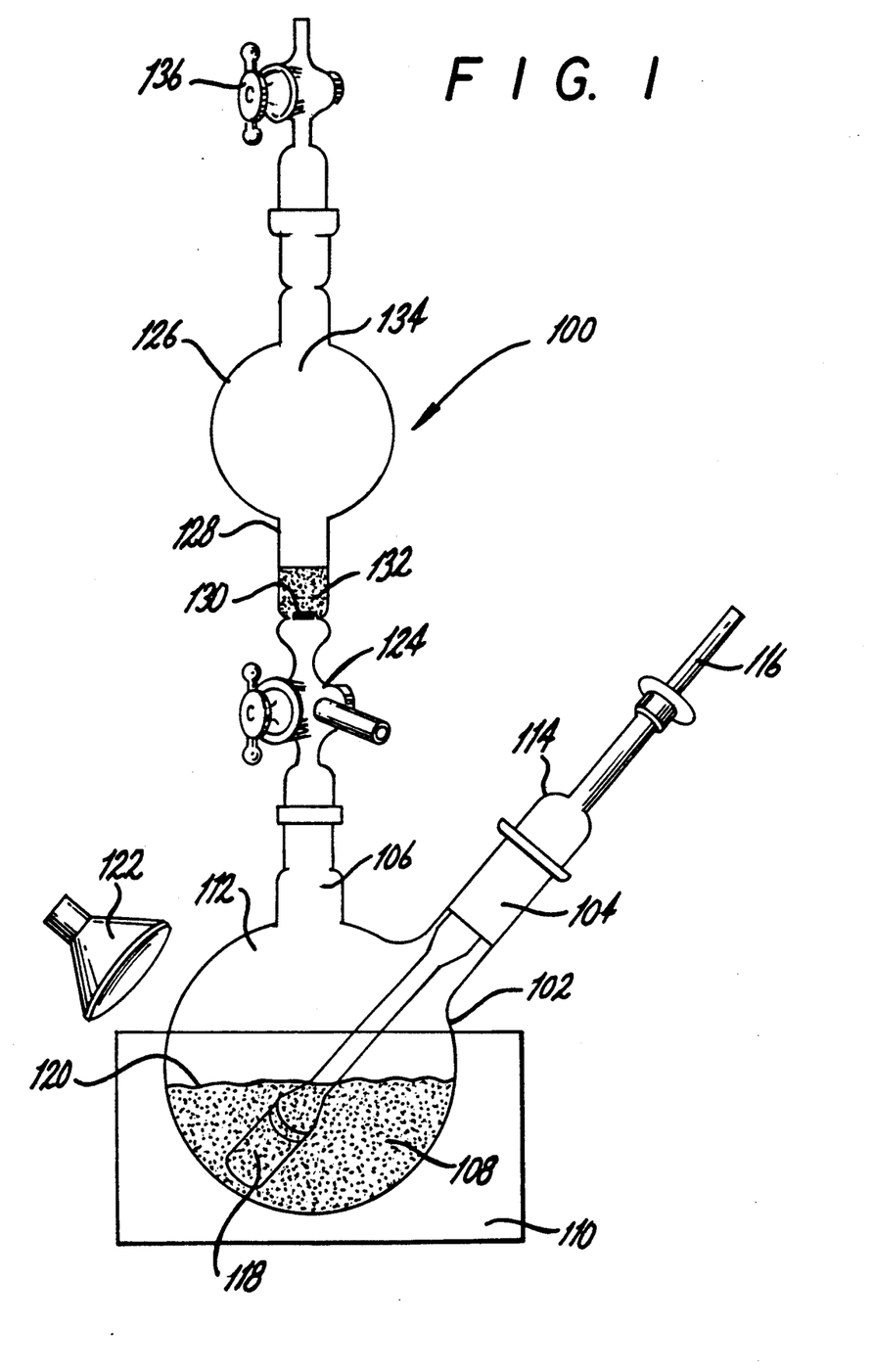
FIG. 1 is a schematic representation of an apparatus for recovering at least one solute from a liquid menstruum in accordance with this invention wherein the at least one solute is recovered in an organic solvent.

With respect to FIG. 1, a separator system 100 is provided which comprises glass sample vessel 102 having neck 104 and neck 106. The vessel 102 is adapted to contain a liquid menstruum 108. As depicted, the portion of vessel 102 containing liquid menstruum 108 is positioned within sonic bath 110 which aids in the dispersion of gas through the liquid menstruum. Other means of agitation such as stirring or pumping the liquid menstruum can alternatively or in combination be used. Above the liquid menstruum within vessel 102 is vapor space 112.

Vessel 102 is fitted with sparger 114 which enters the vessel through neck 104. Sparger 114 is hermetically sealed in neck 104 such that gas does not escape from vessel 102. Sparger 114 comprises gas inlet line 116 which provides for gas communication from the outside to the inside of vessel 102. The sparger has at the end inside vessel 102 a gas distribution means 118 (e.g., a coarse glass frit) which is positioned entirely below the top surface 120 of liquid menstruum 108. The gas distribution means serves to provide the gas (e.g., helium) in finely-divided bubbles. The finely-divided bubbles pass to vapor space 112 and entrain liquid menstruum. Infrared lamp 122 is adapted to shine through the glass of vessel 102 and provide energy to the entrained liquid.

As depicted, vessel 102 has neck 106 positioned axially above the liquid menstruum. Neck 106 is fitted with vent valve 124 which provides for communication of vapor within the vapor space to analyte trap 126. The analyte trap has a lower portion 128 which contains a coarse glass frit plate 130 which permits vapor to rise through it but not allow liquid to rapidly seep through it. The lower portion of the analyte trap is adapted to hold solvent 132 for the analyte (e.g., methylene chloride) such that the vapor passing through glass frit plate 130 contacts solvent 132. Above the lower portion 128 is a condenser portion 134 of the analyte trap. As depicted in FIG. 1, the condenser Portion is an air condenser. Alternatively, water condenser or other type of condenser may be used. The condenser portion is adapted to condense vaporized solvent, if any, and analyte, such that they are retained within solvent 132. The condenser portion 134 of the analyte trap is in communication with valve 136 through which vapor exits the system. Valve 136 serves as a flow restrictor to avoid undue loss of vapor from the system.

A sample of solvent 132 containing the analyte can be used as a sample for, e.g., gas chromatography. Often, vacuum distillation or other means for concentrating the sample can be used prior to the analytical analysis. Frequently, this further concentration can be readily effected due to the nature of the recovered product provided by the methods of this invention.

Figure 2:
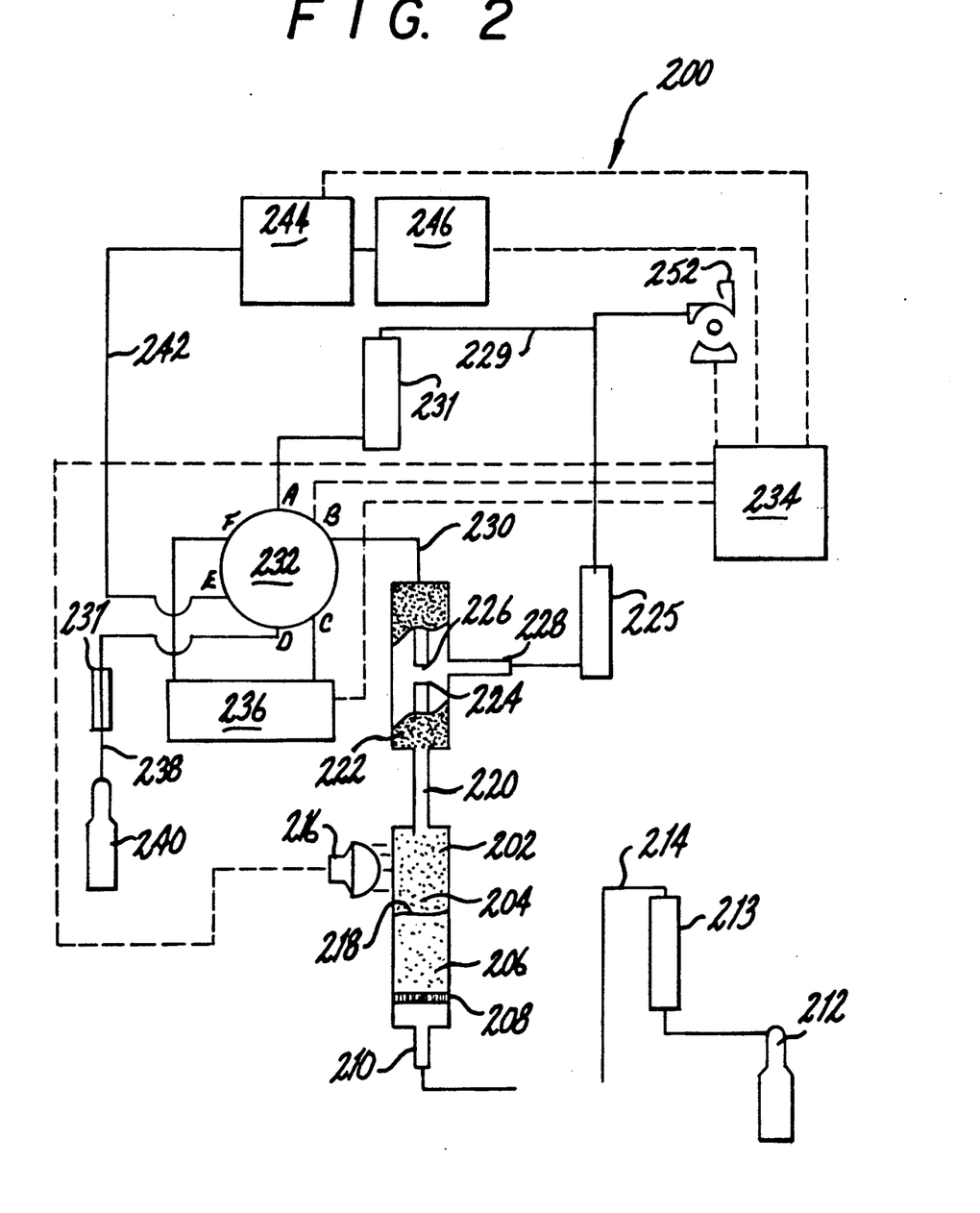
FIG. 2 is a schematic representation of an analytical apparatus in accordance with this invention in which a momentum separator is used.

With respect to FIG. 2, an analytical system 200 is provided with glass vessel 202 which is adapted to contain vapor space 204 above liquid menstruum 206. At the bottom of vessel 202 is coarse glass frit plate 208 with gas entry port 210 at the bottom of vessel 202. The glass frit plate retains the liquid menstruum from passing to gas entry port 210 but permits gas to enter the liquid menstruum as finely-divided bubbles. As shown, helium from tank 212 passes through line 214 containing flow controller 213 to gas entry port 210.

Infrared lamp 216 is adapted to shine through the glass wall of vessel 202 to provide energy to the analyte in the entrained liquid carried above the top surface 218 of the liquid menstruum by the gas bubbles. The vapor from vapor space 204 exits vessel 202 via line 220 and passes to momentum separator 222 having spaced apart projecting orifice 224 and target orifice 226. Adjacent to the space between the orifices 224 and 226 and positioned on the side of momentum separator 222 is vacuum line 228 which provides a transverse force to assist in deflecting lighter molecules from the projected path. Vacuum line 228 is in fluid communication with vacuum pump 252 and contains flow controller 225. Vacuum pump 252 may contain immediately upstream a cold trap for protection purposes.

The concentrated effluent from momentum separator 222 exits via line 230 and passes to switching valve 232. Switching valve 232 is shown as having six ports (A, B, C, D, E and F) and is in communication with computer 234 which, among other things, controls the passing of fluid between the ports. Port A is in fluid communication with vacuum pump 252 via line 229 containing flow controller 231. Port B is in communication with line 230 containing the concentrated effluent from momentum separator 222. Ports C and F are in communication with each end of cryogenic focusing device 236. Cryogenic focusing device 236 is adapted to freeze vaporous analytes and solvents and then be heated to selectively vaporize the frozen components. The cryogenic focusing device 236 is also in communication with computer 234. Port D is in communication via line 238 having flow controller 237 with helium tank 240. Port E is in fluid communication via line 242 with a gas chromatograph 244 and mass spectrometer 246 (which obtains the output from the gas chromatograph). Both the gas chromatograph and mass spectrometer are in communication with computer 234.

In operation, during a first phase the computer controls the switching valve 232 such that the effluent from the momentum separator passes from port B to port C and through cryogenic focusing device 236 which is operating per instructions from the computer, to freeze analyte and any remaining solvent from the effluent. Helium contained in the analyte-containing gases is not condensed in cryogenic focusing device and exits through port F and passes to the vacuum pump via port A. Also, helium passes from port D to port E to continually purge the gas chromatograph/mass spectrometer system.

The switching block operates the same for the second stage with the changes as noted below.

In the second stage, port B communicates with port A and thus the vapors passing through the momentum separator are directed to the vacuum pump. Helium is passed from port D to port C to be passed through the cryogenic focusing device 236. The cryogenic focusing device is heated sufficiently to vaporize the analyte. Helium and eluted analyte are removed via port F to port E and then directed through the gas chromatograph/mass spectrometer system.

In the fourth stage, the switching block operates the same as in the second stage but the cryogenic focusing device 236 is heated and purged with helium to clean the device of analyte and solvent.

The following examples are provided in further illustration of the invention and are not in limitation thereof. All parts and percentages of solids are by weight and all parts and percentages of liquids and gases are by volume unless otherwise indicated.

EXAMPLE 1

The apparatus generally described in FIG. 1 is used to detect certain analyte samples placed in water and in soil samples in levels of 100 parts per billion (ppb) by weight per liter of water or kilogram of soil. The soil for the samples is obtained from a chemical plant site in Brownsville, Tex., and thus may contain various of the added analytes.

The capacity of the glass vessel for the apparatus is about 200 milliliters and is a adapted to be agitated with a vortex mixer. A 250 watt infrared bulb (available from General Electric Company, Fairfield, Conn.) is positioned about 10 centimeters from the vessel. The lower neck of the analyte trap has a volume of about 20 milliliters and is fitted with a glass frit plate. The condensor portion of the analyte trap has a radius of about 3 centimeters.

The gas chromatograph is a Model 5890 available from the Hewlett-Packard Corporation, Avondale, Pa., and uses a fused silica capillary column of 30 meters by 0.32 millimeter inside diameter with a one micron liquid phase film thickness of phenyl methyl silicone available as DB-5 from J & W Scientific, Folson, Calif. The injection port temperature is 280° C. and a helium carrier linear velocity of 30 centimeters per second is used. Injection samples of about 2 microliters are used. The mass spectrometer is Model 5970 available from the Hewlett-Packard Corporation, Palo Alto, Calif. The transfer line between the gas chromatograph and mass spectrometer is about 280° C. The mass spectrometer is tuned in accordance with the manufacturer's instructions; however, the electron multiplier voltage is set at 200 volts above the tuning specifications.

The general procedure is that one hundred milliliters are used for water samples and for solid and semi-solid samples, about 10 grams are placed in the vessel and reagent water is added to provide a final volume of 100 milliliters. At this point known amounts of internal standards are added (usually about 50 micrograms per liter of water samples and 0.5 milligrams per kilogram of solid or semisolid sample.) Approximately thirty grams of calcium chloride (if used) is added as a transfer-enhancing agent. Approximately 15 to 20 milliliters of methylene chloride are placed in the analyte trap.

Helium is then passed through the sparger at a rate of about 1000 milliliters per minute and the liquid menstruum is agitated with a vortex mixer operated at a frequency of about 60 hertz. The flow restrictor on the analyte trap serves to reduce the loss of methylene chloride. With the infrared lamp on, the purging operation is continued for about 30 minutes.

The apparatus is dissembled and the analyte trap is back flushed into a sample bottle. The methylene chloride sample contains some water carried with the gases from the vapor space. While under septum seal, the methylene chloride layer is removed by a syringe and needle from the sample bottle and transferred to another sample bottle having a septum seal. The methylene chloride sample is then subjected to vacuum distillation (10 torr, initially at ambient temperature and falls to the boiling point of the methylene chloride) at the pressure to leave approximately 50 microliters of liquid. This liquid is used for the samples to be injected into the gas chromatograph/mass spectrometer assembly.

The procedure is repeated for the analyte compounds listed below with neither the infrared light or calcium chloride (Runs A) (comparative); with no infrared light but with calcium chloride (Runs B) (comparative); with infrared light but no calcium chloride (Runs C) and with both infrared light and calcium chloride (Runs D). The results reported in Table I are for water samples and Table II are for soil samples and the reported numbers are the ion abundance counts (raw data) divided by 1000.

TABLE I

| COMPOUND | A NO IR/SALT | B SALT ONLY | C IR ONLY | D IR & SALT |
| --- | --- | --- | --- | --- |
| 2-BUTANONE | 170 | 900 | 2100 | 750 |
| 2-BUTANOL | 230 | 400 | 850 | 600 |
| ISOPROPYL ETHER | 520 | 630 | 980 | 250 |
| ISOBUTANOL | 76 | 440 | 1100 | 710 |
| METHYL PROPIONATE | 1100 | 2600 | 5400 | 2000 |
| 1,1,1-TRICHLOROETHANE | 750 | 1000 | 1800 | 790 |
| ISOPROPYL ACETATE | 920 | 1900 | 3000 | 1100 |
| N-BUTANOL | 93 | 560 | 1700 | 1800 |
| BENZENE | 4700 | 5200 | 15000 | 3300 |
| 1,4-DIOXANE | 0 | 0 | 1400 | 1700 |
| 2-HEXANONE | 2500 | 7500 | 14000 | 7200 |
| TOLUENE | 2900 | 4000 | 7200 | 3200 |
| 4-METHYL-2-PENTANONE | 1400 | 7300 | 16000 | 8800 |
| CHLOROBENZENE | 4000 | 5900 | 11000 | 5400 |
| ETHYL BENZENE | 1800 | 2800 | 5300 | 2600 |
| P/M-XYLENE | 4800 | 7600 | 14000 | 7100 |
| STYRENE | 3800 | 6700 | 13000 | 7200 |
| O-XYLENE | 2400 | 4000 | 7500 | 3800 |
| PHENOL | 0 | 0 | 340 | 1200 |
| CHLOREX | 180 | 5200 | 8500 | 18000 |
| 1,3-DICHLOROBENZENE | 4400 | 10000 | 19000 | 12000 |
| 1,4-DICHLOROBENZENE | 5300 | 12000 | 21000 | 14000 |
| BENZYL ALCOHOL | 0 | 49 | 67 | 890 |
| 1,2-DICHLOROBENZENE D4 | 4400 | 12000 | 23000 | 15000 |
| 1,2-DICHLOROBENZENE | 5200 | 13000 | 23000 | 15000 |
| TETRAHYDRONAPHTHALENE | 8600 | 27000 | 40000 | 30000 |
| NAPHTHALENE D8 | 13000 | 54000 | 43000 | 63000 |
| NAPHTHALENE | 19000 | 66000 | 57000 | 68000 |
| 2-METHYLNAPHTHALENE | 17000 | 54000 | 44000 | 55000 |
| BIPHENYL | 24000 | 82000 | 39000 | 76000 |
| BIPHENYLETHER | 13000 | 51000 | 66000 | 46000 |
| ACENAPHTHYLENE | 15000 | 55000 | 47000 | 96000 |
| ACENAPHTHENE D10 | 7600 | 43000 | 65000 | 47000 |
| ACENAPHTHENE | 15000 | 68000 | 51000 | 61000 |
| DIBENZOFURAN | 19000 | 99000 | 63000 | 95000 |
| FLUORENE | 12000 | 77000 | 49000 | 76000 |
| PHENANTHRENE D10 | 5900 | 56000 | 43000 | 91000 |
| PHENANTHRENE | 9800 | 77000 | 59000 | 100000 |
| ANTHRACENE | 6400 | 25000 | 58000 | 94000 |
| FLUORANTHENE | 4300 | 20000 | 48000 | 120000 |
| PYRENE | 4100 | 17000 | 47000 | 130000 |
| CHRYSENE | 260 | 1000 | 4600 | 11000 |
| BENZO(A)PYRENE | 90 | 440 | 1100 | 5100 |

| COMPOUND | A NO IR/SALT | B SALT ONLY | C IR ONLY | D IR & SALT |
| --- | --- | --- | --- | --- |
| 2-BUTANOL | 28 | | | 130 |
| ISOPROPYL ETHER | 50 | 72 | 120 | 65 |
| ISOBUTANOL | 17 | 81 | 220 | 150 |
| METHYL PROPIONATE | 190 | 440 | 750 | 370 |
| 1,1,1-TRICHLOROETHANE | 100 | 150 | 220 | 160 |
| ISOPROPYL ACETATE | 140 | 230 | 300 | 240 |
| N-BUTANOL | 39 | 86 | 280 | 400 |
| BENZENE | 570 | 1100 | 1300 | 900 |
| 1,4-DIOXANE | | 61 | 170 | 350 |
| 2-HEXANONE | 410 | 1200 | 2000 | 1600 |

-continued

| COMPOUND | A<br>NO IR/SALT | B<br>SALT ONLY | C<br>IR ONLY | D<br>IR & SALT |
|---|---|---|---|---|
| TOLUENE | 410 | 590 | 940 | 620 |
| 4-METHYL-2-PENTANONE | 350 | 1300 | 2200 | 1500 |
| CHLOROBENZENE | 530 | 880 | 1500 | 880 |
| ETHYL BENZENE | 250 | 420 | 700 | 440 |
| P/M-XYLENE | 690 | 1000 | 1900 | 900 |
| STYRENE | 560 | 1000 | 1800 | 1100 |
| O-XYLENE | 350 | 600 | 990 | 620 |
| PHENOL | | | 59 | 140 |
| CHLOREX | 70 | 610 | 2200 | 1900 |
| 1,3-DICHLOROBENZENE | 710 | 1400 | 2600 | 1300 |
| 1,4-DICHLOROBENZENE | 820 | 1700 | 3100 | 1600 |
| BENZYL ALCOHOL | | | | 49 |
| 1,2-DICHLOROBENZENE D4 | 740 | 1900 | 3300 | 1600 |
| 1,2-DICHLOROBENZENE | 870 | 1800 | 3300 | 1600 |
| TETRAHYDRONAPHTHALENE | 1400 | 3200 | 5800 | 3000 |
| NAPHTHALENE D8 | 2500 | 7500 | 12000 | 5900 |
| NAPHTHALENE | 3300 | 8000 | 14000 | 6800 |
| 2-METHYLNAPHTHALENE | 3200 | 6900 | 11000 | 5200 |
| BIPHENYL | 5200 | 11000 | 17000 | 7500 |
| BIPHENYLETHER | 3300 | 7300 | 10000 | 4600 |
| ACENAPHTHYLENE | 3700 | 13000 | 21000 | 9500 |
| ACENAPHTHENE D10 | 2000 | 7100 | 9700 | 4300 |
| ACENAPHTHENE | 3400 | 9200 | 13000 | 6500 |
| DIBENZOFURAN | 4800 | 15000 | 21000 | 10000 |
| FLUORENE | 3000 | 5200 | 8000 | 8000 |
| PHENANTHRENE D10 | 1400 | 7600 | 15000 | 11000 |
| PHENANTHRENE | 2400 | 9200 | 22000 | 13000 |
| ANTHRACENE | 1600 | 4200 | 22000 | 13000 |
| FLUORANTHENE | 660 | 2000 | 14000 | 14000 |
| PYRENE | 560 | 1600 | 13000 | 14000 |
| CHRYSENE | 32 | 100 | 1000 | 1100 |
| BENZO(A)PYRENE | | | 130 | 120 |

EXAMPLE 2

The procedure generally described in Example 1 is repeated except that an Incos 50 gas chromatograph/mass spectrometer (available from Finnigan MAT, San Jose, Calif.) is used. The gas chromatograph is temperature programmed (40° C. for four minutes, then 10° C. increases per minute to 290° C. maximum). The mass spectrometer uses electron input ionization and is operated with a scan range of 35 to 500 atomic mass units with one scan per second. The tuning is in accordance with the United States Environmental Protection Agency guidelines SW-846 Method 8270, third edition, specifications for decafluorotriphenylphosphine. Autoquam Software Revision 9.00 of Dec. 30, 1988 (available from Finnigan MAT) is used for identification of compounds and amounts.

A soil sample obtained from a chemical plant site at Ponce, Puerto Rico is divided into nine aliquots of about 10 grams each and each is spiked with 0.5 milligrams per kilogram of each of the compounds listed on Table III together with 10 internal standards: Acenaphthene-d10, Bromochloromethane, Chlorobenzene-d5, Chrysene-d12, 1,4-Dichlorobenzene-d45, 1,4-Difluorobenzene, Naphthalene-d8, Perylene-d12, Phenanthrene-d10, and Phenol-d6. For each run, ten grams of the sample are slurried in 100 milliliters of 30 percent aqueous calcium chloride solution. The purging and trapping in methylene chloride continues for about thirty minutes. The infrared lamp is about 10 centimeters from the glass flask during the purging. Prior to removing the methylene chloride and water from the analyte trap, about 0.25 milliliter of 11.6 molar aqueous hydrochloric acid is added to the methylene chloride to ensure that acidic analytes, such as phenol compounds, are partitioned to the methylene chloride phase. The methylene chloride from the analyte trap is evaporated as in Example 1 to about 50 microliters, and liquid aliquots of 1 microliter are injected into the gas chromatograph. This procedure is repeated for each of the nine samples.

The internal standard is assumed to be recovered in an amount of 0.5 milligrams per kilogram of soil sample and the comparative quantitation ion of the analyte is converted to milligrams per kilogram relative to the internal standard s quantitation ion. Table III reports the results of the analytical procedure in terms of the average recovery percentage: (determined concentration/added concentration)×100 for the nine samples and percent standard deviation: (standard deviation/mean determined concentration)×100 for the nine samples. The recovery from the nine samples are averaged and reported as average recovery, in weight percent. Also reported is the standard deviation of the nine samples, in weight percent. Table III further reports two acceptable ranges for recoveries and standard deviations for each analyte pursuant to the United States Environmental Protection Agency guidelines SW-846, supra. Using this method, 2,4,6-tribromophenol is not satisfactorily recovered.

TABLE III

| COMPOUND: | AVERAGE RECOVERY, % | % STD. DEV. | TARGET RECOVERY RANGE %, WATER (SOIL) | TARGET % STD. DEV. |
|---|---|---|---|---|
| 1,2-DICHLOROETHANE-D4 | 104 | 11 | 76-114 (70-121) | NA** |
| TOLUENE-D8 | 96 | 9 | 88-110 (81-117) | NA |
| 2-FLUOROPHENOL | 87 | 50 | 21-100 (25-121) | NA |
| BROMOFLUOROBENZENE | 106 | 4 | 86-115 (74-121) | NA |

TABLE III-continued

| COMPOUND: | AVERAGE RECOVERY, % | % STD. DEV. | TARGET RECOVERY RANGE %, WATER (SOIL) | TARGET % STD. DEV. |
|---|---|---|---|---|
| NITROBENZENE-D5 | 146 | 19 | 35-114 (23-120) | NA |
| 2-FLUOROBIPHENYL | 85 | 20 | 43-116 (30-115) | NA |
| TERPHENYL-D14 | 135 | 23 | 33-141 (18-137) | NA |
| 1,2-DICHLOROETHANE | 150 | 9 | 49-155 | 30.0 |
| BENZENE | 155 | 60 | 37-151 | 34.5 |
| TOLUENE | 164 | 22 | 47-150 | 24.0 |
| ETHYLBENZENE | 151 | 19 | 37-162 | 37.5 |
| M & P-XYLENE | 153 | 21 | NA | NA |
| O-XYLENE | 154 | 19 | NA | NA |
| PHENOL | 83 | 15 | 5-112 | 22.6 |
| ACETOPHENONE | 159 | 30 | NA | NA |
| 2,4-DIMETHYLPHENOL | 87 | 25 | 32-119 | 26.1 |
| NAPHTHALENE | 114 | 13 | 21-133 | 30.1 |
| ACENAPHTHYLENE | 117 | 18 | 33-145 | 40.2 |
| ACENAPHTHENE | 103 | 20 | 47-145 | 27.6 |
| BUTYLATED HYDROXYTOLUENE (BHT) * | 82 | 102 | NA | NA |
| DIETHYL PHTHALATE | 88 | 33 | D-114 | 26.5 |
| FLUORENE | 101 | 31 | 59-121 | 20.7 |
| PHENANTHRENE | 87 | 7 | 54-120 | 20.6 |
| ANTHRACENE | 89 | 9 | 27-133 | 32.0 |
| DI-N-BUTYL PHTHALATE | 67 | 19 | 1-118 | 16.7 |
| FLUORANTHENE | 68 | 21 | 26-137 | 32.8 |
| PYRENE | 151 | 44 | 52-115 | 25.2 |
| CHRYSENE | 72 | 39 | 17-168 | 48.3 |
| BENZO(A)ANTHRACENE | 72 | 22 | 33-143 | 27.6 |
| DI-N-OCTYL PHTHALATE * | 3 | 121 | 4-146 | 31.4 |
| BENZO(A)PYRENE | 20 | 62 | 17-163 | 39.0 |
| STYRENE | 153 | 17 | NA | NA |
| TETRAHYDRONAPHTHALENE | 112 | 18 | NA | NA |
| 2-METHYLNAPHTHALENE | 111 | 13 | NA | NA |

* Corrected for unspiked samples.
**NA means no value reported by the Environmental Protection Agency.

EXAMPLE 3

A sample of water containing added analytes is analyzed using an apparatus similar to that described in FIG. 2. The separation vessel is about 200 milliliters in capacity and has a porous glass frit plate. The separation vessel has an upper and lower neck, each about 2.5 centimeters in diameter and about 7 centimeters in length, extending axially from a spherical midsection having a diameter of about 7.6 centimeters in diameter. An infrared lamp (250 watt available from the General Electric Company, Fairfield, Conn.) is positioned about 10 centimeters from the separation vessel. The momentum separator contains two glass tubes, each about 0.64 centimeters outside diameter axially positioned and spaced apart about 1 millimeter. The projecting tube has a 0.5 millimeter inside diameter and the receiving tube, a 0.25 millimeter diameter. The end of each tube is at a right angle and not tapered. The cryogenic focusing device is Model 16200 available from Chrompack Inc., Raritan, N.J. The gas chromatograph and mass spectrometer are those described in Example 1 and are operated in substantially the same manner. The piping from the momentum separator to the gas chromatograph is contained with an oven at about 280° C.

A one-hundred milliliter water sample is spiked with the analytes set forth in Table IV and is placed in the separation vessel with 15 grams of calcium chloride. A helium purge flow rate of 110 milliliters per minute is used. The vacuum on the momentum separator is adjusted such that 100 milliliters of gas are removed per minute and 10 milliliters per minute pass through the momentum separator. The cryogenic focusing device operates at about −50° C. and is heated to about 280° to 300° when removing the analytes. Each cryogenic cycle is for about 20 minutes. The analytical results are presented in Table IV.

The momentum separator and switching valve and intermediate piping are enclosed in a heated oven (280° C.). The outlet from the cryogenic focusing device is mounted in the oven. The piping from the switching valve and the inlet of the cryogenic focuser is maintained at 280° C. by means of a heated transfer line. Likewise the piping from the switching valve and the gas chromatograph is maintained at 280° C. by means of a heated transfer line.

TABLE IV

| COMPOUND | ION ABUNDANCE | ION MEASURED |
|---|---|---|
| 1,1,1-TRICHLOROETHANE | 642 | 97 |
| 1,3-DICHLOROBENZENE | 2370 | 146 |
| 1,4-DICHLOROBENZENE | 5570 | 146 |
| 1,4-DIOXANE | 2000 | 88 |
| 2,4,6-TRICHLOROPHENOL | 22500 | 196 |
| 2,4-DICHLOROPHENOL | 13500 | 162 |
| 2,4-DIMETHYLPEHNOL | 4570 | 122 |
| 2-BUTANOL | 3410 | 31 |
| 2-CHLOROPHENOL | 4720 | 128 |
| 2-HEXANONE | 2890 | 43 |
| 2-METHYL NAPHTHALENE | 67000 | 142 |
| 2-METHYL-4,6-DINITROPHENOL | 39 | 198 |
| 2-NITROPHENOL | 10900 | 139 |
| 4-CHLORO-3-METHYL PHENOL | 2260 | 107 |

TABLE IV-continued

| COMPOUND | ION ABUNDANCE | ION MEASURED |
| --- | --- | --- |
| 4-METHYL-2-PENTANONE | 3600 | 43 |
| ACENAPHTHENE | 70500 | 154 |
| ACENAPHTHYLENE | 92800 | 152 |
| ANTHRACENE | 88300 | 179 |
| BENZENE | 11200 | 78 |
| BENZYL ALCOHOL | 4150 | 108 |
| BIPHENYL | 86100 | 154 |
| BIPHENYL ETHER | 47200 | 170 |
| BIS(2-CHLOROETHYL)ETHER | 12500 | 93 |
| CHLOROBENZENE | 14000 | 112 |
| CHRYSENE | 315 | 228 |
| DI 2-ETHYL HEXYL PHTHALATE | 2510 | 149 |
| DI N-BUTYL PHTHALATE | 12400 | 149 |
| DI N-OCTYL PHTHALATE | 44000 | 149 |
| DIBENZOFURAN | 94700 | 168 |
| ETHYL BENZENE | 5910 | 106 |
| FLUORANTHENE | 1040 | 202 |
| FLUORENE | 79200 | 166 |
| TETRAHYDRONAPHTHALENE | 27800 | 104 |
| M-XYLENE | 7070 | 106 |
| METHYL ETHYL KETONE | 1790 | 72 |
| METHYL PROPIONATE | 4350 | 57 |
| N-BUTANOL | 5150 | 31 |
| NAPHTHALENE | 90400 | 128 |
| O-XYLENE | 7540 | 106 |
| P-XYLENE | 7070 | 106 |
| PENTACHLOROPHENOL | 15700 | 266 |
| PHENANTHRENE | 99400 | 178 |
| PHENOL | 4110 | 94 |
| PYRENE | 1140 | 202 |
| STYRENE | 13300 | 104 |
| TOLUENE | 10800 | 92 |
| 1,2-DICHLOROBENZENE | 17300 | 146 |

It is claimed:

1. A process for extracting at least one solute from a liquid menstruum in which at least one solute tends to be at a higher concentration at an interface of said menstruum with a gas than in the menstruum as a whole, comprising passing through the menstruum a gas in the form of finely-divided bubbles while the menstruum is at a temperature below its boiling point, said bubbles forming an interface with and passing from the menstruum into an immediately adjacent vapor space and entraining some of said menstruum; irradiating the vapor space from a radiation source proximate to the vapor space at least in the portion of the vapor space containing said entrained menstruum with electromagnetic radiation which imparts energy to the at least one solute in an amount sufficient to maintain at least a portion of the at least one solute contained in the entrained menstruum in the vapor space and withdrawing from said vapor space a vapor stream comprising the gas passed through the menstruum and the at least one solute.

2. The process of claim 1 wherein the electromagnetic radiation comprises at least one of radio wave radiation, microwave radiation and infrared radiation.

3. The process of claim 1 wherein the liquid menstruum comprises water.

4. The process of claim 3 wherein said at least one solute is organic.

5. The process of claim 4 wherein the liquid menstruum contains transfer enhancing agent.

6. The process of claim 4 wherein the electromagnetic radiation comprises at least one of radio wave radiation, microwave radiation and infrared radiation.

7. The process of claim 6 wherein the electromagnetic radiation comprises infrared radiation.

8. The process of claim 1 wherein the gas comprises at least one of air, nitrogen and helium.

9. The process of claim 1 wherein the liquid menstruum contains transfer enhancing agent.

10. A process for extracting at least one solute from a liquid menstruum in which the at least one solute tends to be at a higher concentration at an interface of the menstruum with a gas than in the menstruum as a whole, comprising passing through the menstruum a gas in the form of finely-divided bubbles while the menstruum is at a temperature below its boiling point, said bubbles forming an interface with and passing from the menstruum into an immediately adjacent vapor space and entraining some of said menstruum; irradiating the vapor space at least in the portion of the vapor space containing entrained menstruum, with an electromagnetic radiation which imparts energy to the at least one solute in an amount sufficient to maintain at least a portion of the at least one solute contained in the entrained menstruum in the vapor space; and recovering at least a portion of the at least one solute.

11. The process of claim 10 wherein the recovery of the solute is by at least one of adsorption and absorption.

12. The process of claim 10 wherein the, liquid menstruum is purified of said at least one solute.

13. The process of claim 10 wherein the recovered at least a portion of the at least one solute is concentrated.

14. The process of claim 13 wherein the concentrated recovered at least a portion of the at least one solute is analyzed.

15. The process of claim 10 wherein the recovered at least a portion of the at least one solute is analyzed.

16. The process of claim 10 wherein the liquid menstruum contains transfer enhancing agent.

17. A method for analyzing a menstruum from the presence of at least one solute which, in said menstruum tends to be at a higher concentration at an interface of the menstruum with a gas than in the menstruum as a whole comprising passing a gas in the form of finely-divided bubbles through the menstruum, said bubbles forming an interface with and passing from the menstruum into an immediately adjacent vapor space and entraining some of said menstruum; indicating the vapor space at least in the portion of the vapor space containing said entrained menstruum with an electromagnetic radiation which imparts to the at least one solute in an amount at least sufficient to maintain at least a portion of the at least one solute contained in the entrained menstruum in the vapor space; withdrawing from the vapor space a vapor stream comprising the gas passed through the menstruum and at least one solute; and subjecting at least a portion of the vapor stream to an analytical procedure to ascertain at least one of the presence and relative concentration of the at least one solute.

18. The method of claim 17 wherein the analytical procedure comprises at least one of chromatography, mass spectroscopy, infrared spectroscopy, wet chemical analysis and colorimetric analysis.

19. The method of claim 18 wherein the electromagnetic radiation comprises at least one of radio wave radiation, microwave radiation and infrared radiation.

20. The method of claim 19 wherein the electromagnetic radiation comprises infrared radiation.

21. The method of claim 18 wherein the liquid menstruum comprises water.

22. The method of claim 21 wherein said at least one solute is organic.

23. The method of claim 22 wherein the liquid menstruum comprises transfer enhancing agent.

24. The method of claim 22 wherein the gas comprises at least one of air, nitrogen and helium.

25. The method of claim 24 wherein the gas comprises helium.

26. The method of claim 17 wherein the withdrawn vapor stream containing the at least one solute is concentrated prior to the analytical procedure.

27. The method of claim 26 wherein the concentration of the solute is effected by at least a momentum separator.

28. The method of claim 27 wherein subsequent to the momentum separator, the at least one solute is further concentrated by a cryogenic focusing device.

29. The method of claim 26 wherein the concentration of the at least one solute is effected by at least a cryogenic focusing device.

30. The method of claim 17 wherein the liquid menstruum contains a transfer enhancing agent.

* * * * *